United States Patent [19]

Pope et al.

[11] Patent Number: 5,399,501

[45] Date of Patent: Mar. 21, 1995

[54] COVALENT ATTACHMENT OF SPECIFIC BINDING MEMBERS TO A SOLID PHASE WITH TWO BIFUNCTIONAL REAGENTS AND A DITHIO COMPOUND

[75] Inventors: Mark R. Pope, Wildwood; Kevin M. Knigge, Gurnee, both of Ill.

[73] Assignee: Abbott Laboratories, Abbott Park, Ill.

[21] Appl. No.: 852,837

[22] Filed: Mar. 16, 1992

Related U.S. Application Data

[63] Continuation of Ser. No. 346,108, May 2, 1989, abandoned.

[51] Int. Cl.$^6$ ............... G01N 33/549; G01N 33/543; C12N 11/06; C12N 11/00
[52] U.S. Cl. .................... 436/532; 435/174; 435/181; 435/974; 436/518; 436/811; 530/810; 530/816
[58] Field of Search ............. 435/181, 174, 974; 436/532, 518, 811; 530/816, 810

[56] References Cited

U.S. PATENT DOCUMENTS

| | | | |
|---|---|---|---|
| 4,176,006 | 11/1979 | Cormier et al. | 435/74 |
| 4,237,267 | 12/1980 | Okuyama et al. | 536/1 |
| 4,529,712 | 7/1985 | Jou et al. | 436/519 |
| 4,886,755 | 12/1989 | Ngo | 435/181 X |

(List continued on next page.)

FOREIGN PATENT DOCUMENTS

| | | |
|---|---|---|
| 0227351A3 | 12/1986 | European Pat. Off. |
| 0306943A3 | 9/1988 | European Pat. Off. |
| 0314127A3 | 10/1988 | European Pat. Off. |
| 2917001A1 | 4/1979 | Germany |

OTHER PUBLICATIONS

Kincaid, et al., "Affinity Chromatography of Brain Cyclic Nucleotide Phosphodiesterase Using 3-(2-Substituted Calmodulin Linked to Thiol-Sepharose", *Biochemistry*, 22(4):826–830 (1983).

Jonsson, et al., "Immobilization of Immunoglobulins on Silica Surfaces (Stability)", *Biochem. J.*, 227:363–371 (1985).

Jonsson, et al., "Immobilization of Immunoglobulins on Silica Surfaces (Kinetics of Immobilization and Influence of Ionic Strength)", *Biochem. J.*, 227:373–378 (1985).

Bhatia, et al., "Use of Thiol-Terminal Silanes and Heterobifunctional Crosslinkers for Immobilization of Antibodies on Silica Surfaces", *Analytical Biochemistry*, 178:408–413 (1989).

*BioRad Catalog*, Mar. 1988, Page 59 describing "Affi-Gel 401 Sulfhydryl Get".

Cautrecasas, P. *J. Biolog. Chem* 245(12):3059–3065 (1970).

(List continued on next page.)

*Primary Examiner*—David M. Naff
*Attorney, Agent, or Firm*—Thomas D. Brainard

[57] ABSTRACT

A specific binding member such as an antigen or antibody is immobilized by covalent attachment to a solid phase such as a latex microparticle. The solid phase is reacted with a heterobifunctional or homobifunctional coupling agent to form a complex that is then reacted with a dithiol compound to form a thiolated solid phase. A specific binding member is reacted with the coupling agent to form a complex which is then reacted with the thiolated solid phase to link the specific binding member to the solid phase through thioethers. Alternatively, the dithiol compound may be reacted with the specific binding member/coupling agent complex to form a thiolated complex that is reacted with the solid phase/coupling agent complex. The coupling agent may contain a spacer. In another embodiment, the solid phase is reacted with a disulfide compound to form a complex and the complex is reacted with a reductant to form a thiolated solid phase which is reacted with a specific binding member/coupling agent complex. The immobilized specific binding member can be used in diagnostic binding assays, and it has increased sensitivity, specificity and stability, while requiring the use of less specific binding member.

26 Claims, 4 Drawing Sheets

U.S. PATENT DOCUMENTS 4,889,916 12/1989 Packard et al. ............... 435/181 X
4,894,229 1/1990 Polson et al. ................... 435/181
5,002,883 3/1991 Bienoarz et al. ................ 435/176

OTHER PUBLICATIONS

Abstract JP-55 136261 (Toyo Jozo; same priority appln as DE-A-2917001.
Abstract (Derwent) WO 87/04171 (Teijin).
Ngo. Applied Biochemistry and Biotechnology, 13:213–219 (1986).
Ngo. Applied Biochemistry and Biotechnology, 13:207–212 (1986).
Yoshitake, et al. Analytical Letters, 15(B2), 147–160 (1982).
O'Sullivan, et al., Analytical Biochemistry, 100:100–108 (1979).
Jue, et al, Biochemistry, 17:25, pp. 5399–5406 (1978).
The Pierce BioResearch Products Technical Bulletin (1983).
Weitman, et al, BioTechniques, pp. 148–152, Sep.–Oct. (1983).

Activation of a Specific Binding Member Using a Maleimido-NHS Active Ester Heterobifunctional Reagent

FIG. 1

Activation of a Specific Binding Member Using an Active Halogen-NHS Active Ester Heterobifunctional Reagent

Modification of an Aminated Solid Phase and Reduction of Disulfide Group

FIG. 5

Modification of Carboxylated Solid Phase and Reduction of Disulfide Group

COVALENT ATTACHMENT OF SPECIFIC BINDING MEMBERS TO A SOLID PHASE WITH TWO BIFUNCTIONAL REAGENTS AND A DITHIO COMPOUND

This application is a Continuation of application Ser. No. 07/346,108, filed May 2, 1989, now abandoned.

BACKGROUND OF THE INVENTION

1. Field of the Invention

The present invention relates to methods and reagents for the covalent attachment of specific binding members to a solid support. In particular, the invention relates to the immobilization of specific binding members on solid supports for use in diagnostic assays and separation procedures. The present invention is also related to the co-owned and copending patent application entitled "Method for Renaturing Proteins in the Presence of Alkyl Sulfate Detergents", filed concurrently herewith and incorporated by reference herein.

2. Description of Related Art

Binding assays have found widespread application in the field of clinical diagnostics for the detection and/or measurement of drugs, hormones, proteins, peptides, metabolites, microorganisms and other substances of interest, commonly referred to as analytes, in both biological and non-biological fluids. Binding assays incorporate specific binding members, typified by antibody and antigen immunoreactants, wherein one member of the specific binding pair is labeled with a signal-producing compound (e.g., an antibody labeled with an enzyme; a fluorescent compound; a chemiluminescent compound; a radioactive label; a direct visual label; etc.). For example, in a binding assay the test sample suspected of containing analyte can be mixed with a labeled anti-analyte antibody and incubated for the immunoreaction to occur. The reaction mixture is subsequently analyzed to detect either the label associated with an antibody/analyte complex (bound label) or the labeled antibody which is not complexed with analyte (free label), thereby enabling the detection or measurement of the analyte in the test sample.

Binding assays can be divided into two general categories known as homogeneous and heterogeneous assays. In the homogeneous assays, the signal produced by the bound label is different from the signal produced by the free label. As a result, bound and free label can be distinguished without physical separation of the individual reactants from the reaction mixture. A well-known homogeneous binding assay is the enzyme-multiplied immunoassay technique (EMIT) which is disclosed in U.S. Pat. No. 3,817,837. In the EMIT assay, the analyte present in the patient's test sample and an enzyme-labeled analyte compete for a limited amount of anti-analyte antibody. The specific binding of the antibody to the analyte-enzyme conjugate modulates the conjugate's enzymatic activity such that the enzyme activity is proportional to the amount of analyte in the test sample. Homogeneous binding assays have the advantages of being rapid, easy to perform, and readily adapted to automation. Their disadvantages are that they are susceptible to interferences caused by non-analyte substances in the test sample, they are generally limited to assays for low molecular weight analytes, and they have a limited sensitivity.

In a heterogenous binding assay, the signal produced by the bound label is indistinguishable from the signal produced by the free label; therefore, the free label and the bound label must be separated from one another to distinguish between their respective signals. In some cases, the complex with which the bound label is associated will substantially differ in molecular weight from the free labeled reactant so that centrifugation can be used to separate the heavier complex.

An alternative to centrifugation involves attaching at least one of the binding assay's reactants to a solid support. The solid support can then be separated from the test sample and the remaining assay reagents to provide for the separation of the free and bound label. The separation of the solid support and reaction mixture can be accomplished either by drawing-off the remaining reaction mixture or by physically removing the solid phase from the reaction mixture. The solid support can also be treated or washed to remove interfering substances prior to the detection or measurement of the label associated with the solid phase.

Longer incubation times may be-required in the heterogeneous assay. This is because the kinetics of a reaction between a solid phase-bound specific binding member and its complementary binding partner tend to be slower than the kinetics of the same reaction when both binding members are in solution. The heterogeneous assays, however, are in general more sensitive than homogeneous assays and less prone to interferences, because interfering substances can be removed by the wash steps.

Variations to this general solid phase separation scheme have been developed, but they typically involve the binding of the analyte to a specific binding member which is attached to a solid phase. Generally, specific binding members are attached to or immobilized on the solid phase by adsorption or covalent bonding. Adsorption results from the action of the solid phase in attracting and holding the specific binding member. With covalent bonding, the specific binding member and the solid phase are chemically reacted to result in a bond which immobilizes the specific binding member on the solid phase.

The linkage between the solid phase and the immobilized specific binding member can greatly affect the binding of that specific binding member to the analyte. For example, antibodies have extremely specific structural, spatial and polar configurations which enable them to recognize and bind to a specific analyte (e.g., antigen). When antibodies are used in an assay for the detection of antigens, the antibodies may be the specific binding members linked to the solid phase. The proximity of the solid phase to the antibody, however, can partially or completely block the sites on the antibody to which the antigen binds. In addition, the linkage between the antibody and the solid phase can alter the conformation of the antibody and thereby affect the antibody's ability to bind to the analyte. The same limitations hold for the linkage of other specific binding members to a solid phase; the specific binding members may attach in a spectrum of positions ranging from complete steric hindrance of the binding site to unhindered access, and/or the conformation of the specific binding member can change upon linking to the solid phase so that its complementary binding partner can no longer recognize it or bind to it. As may be expected, the sensitivity of the assay declines with increasing levels of steric hindrance and loss of reactivity.

A conventional method for covalently attaching a proteinaceous specific binding member to a polymeric solid phase involves the use of carbodiimide to crosslink the amine groups of the protein to the carboxyl groups on the surface of the solid phase. Alternatively, gluteraldehyde is used to crosslink the amines of the protein to surface bound amines on the solid phase. These crosslinking methods, however, are poorly controlled, often resulting in protein/protein crosslinking and nonspecific reactions, such as the over-modification of the protein which may result in a decrease in the binding capacity of the specific binding member. In addition, the protein that is so immobilized has poor reactivity, making it necessary to bind large amounts of the protein to the solid phase to obtain suitable assay sensitivity.

There have been two main approaches to solving the crosslinking problems associated with the heterogeneous assays. One approach has been to complete the reaction of the binding partners prior to the immobilization of the newly formed complex upon the solid phase. The other technique has been to extend the length of the linkage between the specific binding member and the solid phase. The linking or coupling agent must maintain the linkage during the chemical manipulations of the assay, as well as during the physical manipulations of washing and separation steps. Extended length heterobifunctional coupling agents have been described in co-owned and copending patent applications, U.S. Ser. No. 254,288, filed Oct. 11, 1988, now U.S. Pat. No. 5,002,883, and Ser. No. 114,930, filed Oct. 30, 1987, now abandoned, wherein the covalent attachment of specific binding members to the solid phase is accomplished using an extended length molecular chain having at least one linking group that is reactive with a chemical group on the solid phase and at least one linking group that is reactive with a chemical group on the specific binding member.

SUMMARY OF THE INVENTION

The present invention provides methods for preparing thiolated solid phase materials and immobilized specific binding members.

One form of immobilized specific binding member, produced by the present invention, is represented by the formula:

B—R—X—R'—M wherein B is a solid phase having an amino, carboxyl or thiol group. The solid phase is attached to M, an aminated specific binding member, through R and R' which are coupling agents (either heterobifunctional or homobifunctional) and which can be the same coupling agent. The coupling agents are crosslinked through a reaction with X, a dithio compound linked to R and R' through thioethers.

The immobilized specific binding member is prepared by first reacting the solid phase with a first coupling agent, thereby forming a solid phase/coupling agent complex. The aminated specific binding member is reacted with a second coupling agent, thereby forming a specific binding member/coupling agent complex. The solid phase/coupling agent complex is then reacted with a dithiol compound to form a thiolated solid phase/coupling agent complex. And, the thiolated solid phase/coupling agent complex is reacted with the specific binding member/coupling agent complex to form the dithioether crosslinked solid phase/specific binding member complex. Alternatively, the specific binding member/coupling agent complex can be reacted with the dithiol compound to form a thiolated specific binding member/coupling agent complex, which is then reacted with the solid phase/coupling agent complex to form the immobilized specific binding member.

An alternative immobilized specific binding member is represented by the formula:

B—Q—S—R—M wherein B is a solid phase having an amino or carboxyl group, wherein the solid phase is linked to R—M, a specific binding member/heterobifunctional coupling agent complex, by a thiol introducing agent, Q—S. The thiol introducing agents include thiolanes, succinimidyl thioacetates and disulfide compounds which are subsequently reduced to a thiol. This immobilized specific binding member is made by reacting the solid phase with a thiol introducing agent to form a thiolated solid phase; reacting an aminated specific binding member with a heterobifunctional coupling agent, to form a specific binding member/coupling agent complex; and then reacting the thiolated solid phase with the specific binding member/coupling agent complex to form the crosslinked solid phase/specific binding member complex.

The present invention is also of use in forming a thiolated solid phase represented by the formula:

B—R—XH wherein B is a solid phase having an amino, carboxyl or thiol group, R is a heterobifunctional coupling agent and XH is a dithio compound linked to R through a thioether. The thiolated solid phase is made by reacting the solid phase with a heterobifunctional coupling agent to form a solid phase/coupling agent complex and then reacting the complex with a dithiol compound to form a thiolated solid phase/coupling agent complex.

The thiolated solid phase can also be prepared by reacting a solid phase with a disulfide compound to form a solid phase/disulfide complex which is then reacted with a reductant, whereby the disulfide is reduced to form a thiolated solid phase.

The resulting immobilized specific binding member can be used in diagnostic binding assays. And, the immobilized specific binding member can optionally be incorporated into or onto a support medium.

DETAILED DESCRIPTION OF THE INVENTION

The present invention provides novel methods for the covalent linkage of the specific binding member and the solid phase, such as the immobilization of a protein on a solid phase for use in an immunoassay. The method can be used to covalently crosslink two amino-containing components. These components include, but are not limited to, antibodies, enzymes, peptides, cells, haptens, small molecules, solid phases, liposomes, and polymers. The general methodology of the present invention involves the modification of the specific binding member and/or the solid phase to incorporate thiol-reactive functional groups. The activated specific binding member is then allowed to react with the thiolated solid phase to produce the covalent linkage. The specific methodologies of the present invention differ in the means used to introduce the thiol groups to the solid phase. In another aspect of the present invention, both the solid phase and the specific binding member can be individually modified to include extended length heterobifunctional coupling agents, which in turn can be crosslinked through a dithiol compound.

The present invention provides greater control over the chemistry for the production of both derivatized solid supports and immobilized specific binding members. The invention enables the production of immobilized specific binding members which have increased sensitivity, specificity and stability, while requiring less specific binding member be used. In addition, the present invention may alter the surface charge of the solid phase, which in some instances eliminates the charge-related nonspecific interactions which can occur in binding assays. The covalently bound specific binding member/solid phase compounds of the present invention can be used in both sandwich and competitive heterogeneous binding assays, in both forward and reverse assay techniques.

Definitions

The following definitions are applicable to the present invention.

The term "specific binding member", as used herein, refers to a member of a specific binding pair, i.e., two different molecules where one of the molecules through chemical or physical means specifically binds to the second molecule. In addition to antigen and antibody-specific binding pairs, other specific binding pairs include biotin and avidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte. Immunoreactive specific binding members include antigens, haptens, antibodies, and complexes thereof including those formed by recombinant DNA methods or peptide synthesis.

"Analyte", as used herein, is the substance to be detected in or separated from the test sample using the present invention. The analyte can be any substance for which there exists a naturally occurring specific binding member or for which a specific binding member can be prepared. In addition, the analyte may bind to more than one specific binding member. "Analyte" also includes any antigenic substances, haptens, antibodies, and combinations thereof. The analyte can include a protein, a peptide, an amino acid, a hormone, asteroid, a vitamin, a drug including those administered for therapeutic purposes as well as those administered for illicit purposes, a bacterium, a virus, and metabolites of or antibodies to any of the above substances.

"Solid phase", as used herein, includes the material upon which a specific binding member can be immobilized for use in diagnostic assays, affinity chromatography and separation procedures. While the Examples which follow generally deal with microparticle solid phases made of polymeric materials, many other solid phase configurations are possible so long as the material includes or can be formed or derivatized to accept the requisite linking groups enabling the immobilization of a specific binding member.

The solid phase can include, without limitation, polymeric or glass beads, microparticles, tubes, sheets, plates, slides, wells, tapes, test tubes, or the like. Natural, synthetic or naturally occurring materials that are synthetically modified, can be used as the solid phase including polysaccharides, e.g., cellulose materials such as paper and cellulose derivatives such as cellulose acetate and nitrocellulose; silica; silicon particles; inorganic materials such as deactivated alumina, or other inorganic finely divided material uniformly dispersed in a porous polymer matrix, with polymers such as vinyl chloride, vinyl chloride polymer with propylene, and vinyl chloride polymer with vinyl acetate; polyethylene; cloth, both naturally occurring (e.g., cotton) and synthetic (e.g., nylon); porous gels such as silica gel; polymeric films such as polyacrylates; and the like. It will be readily apparent to those skilled in the art that a variety of solid phase materials can be adapted for use in accordance with the present invention.

In addition, a solid phase prepared in accordance with the present invention can be incorporated within or upon a separate support medium. Support media include any suitable absorbent, chromatographic, bibulous, porous or capillary material. For example, the support media can include a fiberglass, cellulose or nylon pad for use in a flow-through assay device as described in co-owned and copending European Patent Publication No. 217,403 published Apr. 8, 1987. The device disclosed therein comprises a substantially planer layer of material having a porous matrix of fibers, upon which are immobilized a plurality of substantially spherical microparticles bearing an immobilized specific binding member. Similarly, a dipstick for a dip and read assay or a test strip for chromatographic (e.g., paper or glass fiber) or thin layer chromatographic (e.g., nitrocellulose) techniques can be used.

The term "test sample", as used herein, includes a naturally occurring or artificially formed liquid test medium suspected of containing the analyte of interest. In diagnostic assays, the test sample is generally a biological fluid or a dilution thereof. Biological fluids from which an analyte can be determined include serum, whole blood, plasma, urine, saliva, amniotic and cerebrospinal fluids, and the like. The reagents and methods of the present invention can also be designed to determine food product and environmental analytes of interest.

The term "coupling agent", as used herein, includes bifunctional crosslinking or coupling agents, i.e., molecules containing two reactive groups or "ends", which may be tethered by a spacer. The reactive ends can be any of a variety of functionalities including, but not limited to: amino reacting ends such as n-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a carboxyl-reactive end, while homobifunctional reagents have two similar reactive ends.

Commercially available heterobifunctional reagents for use in the present invention include, but are not limited to, the maleimido-NHS active esters coupling agents such as m-maleimidobenzoyl-N-hydroxy-succinimide ester (MBS); succinimidyl 4-(N-maleimidomethyl)cyclohexane-1-carboxylate (SMCC); succinimidyl 4-(p-maleimidophenyl)butyrate (SMPB) and derivatives thereof, including sulfosuccinimidyl derivatives such as sulfosuccinimidyl-4-(N-maleimido-methyl) cyclohexane-1-carboxylate (sulfo-SMCC); m-maleimidobenzoyl-sulfosuccinimide ester (sulfo-MBS) and sulfosuccinimidyl 4-(p-maleimido-phenyl)butyrate (sulfo-SMPB).

Other heterobifunctional reagents include the commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl (4-iodoacetyl)aminobenzoate (sulfo-SIAB).

Another group of coupling agents is the heterobifunctional and thiol cleavable agents such as N-succinimidyl 3-(2-pyridylthio)propionate (SPDP). Thiol cleavable agents, such as N,N'-didansyl-L-cystine and L-cystine dimethylester dihydrochloride, can also be used.

Yet another group of coupling agents includes the extended length heterobifunctional coupling agents described in co-owned and copending U.S. patent application Ser. Nos. 254,288 (filed Oct. 11, 1988) and 114,930 (filed Oct. 30, 1987) which are incorporated by reference herein. The extended length heterobifunctional coupling agents include maleimido-NHS active ester reagents wherein the spacer is represented by the formula:

the X is a substituted or unsubstituted amino acid, having from three to ten carbon atoms in a straight chain; n is from one to ten; and R is an alkyl, cycloalkyl, alkyl-cycloalkyl or an aromatic carboxylic ring. The term alkyl-cycloalkyl includes alkyl groups linked to cycloalkyl ring structures where the alkyl group links the cycloalkyl to a maleimide or carbonyl group. The term alkyl includes straight or branched alkyl groups, preferably lower alkyl groups having from one to six carbon atoms.

If a spacer is present to tether the two reactive groups of the coupling agent, the spacer can be any molecular chain that is non-reactive, stable and non-binding to the analyte or other specific binding members with which it will be used. The length of the spacer can be varied and can range from the size of a single atom to the sizes disclosed in U.S. patent application Ser. Nos. 254,288 and 114,930 or larger.

The term "thiol introducing agent", as used herein, includes but is not limited to thiolanes (such as 2-iminothiolane), succinimidyl thioacetates (such as N-succinimidyl-S-acetylthioacetate), and disulfide compounds which are subsequently reduced to a thiol. The thiol introducing agents can be used to activate specific binding members and solid phase materials for their subsequent reaction with a thiol-reactive group.

The choice of a coupling agent or thiol introducing agent depends upon the acceptable performance of that particular agent with the particular solid phase and specific binding member to be used in the diagnostic assay. Therefore, it will be appreciated by those skilled in the art that the coupling agent or thiol introducing agent used in a given assay will generally be determined empirically. In addition, the specific binding member will include one or more amino, carboxyl or thiol groups or can be derivatized by the incorporation of an amino, carboxyl or thiol group thereby enabling the reaction of the specific binding member with a coupling agent or thiol introducing agent. "Activated species" refer to specific binding members and solid phase materials which contain a reactive group through the incorporation of a coupling agent, for example, the activation of a protein with sulfo-MBS. Proteinaceous specific binding members with cysteine residues at the protein's active site can have their activity decreased by the addition of a coupling agent, therefore the cysteine residues in the active site must be protected, by means known in the art, prior to reacting the protein with the coupling agent.

Preparation of Activated or Derivatized Solid Phases and Immobilized Specific Binding Members The general methodology of the present invention involves the modification of a solid phase by the introduction of thiol groups. A specific binding member, e.g., a protein antigen, is also modified to contain thiol-reactive functional moieties such as maleimides or active halogens. The derivatized specific binding member is then added to the thiolated solid phase and reacted to produce a covalent linkage.

Figure 1:
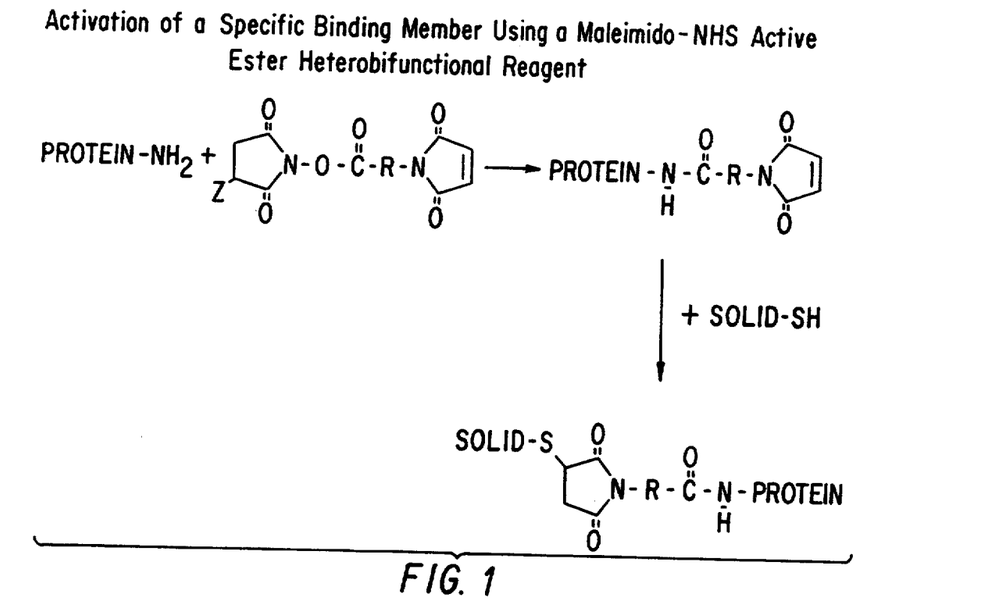
FIG. 1 is a diagrammatical illustration of the modification of an amino-bearing specific binding member to include a thiol-reactive group using a maleimido-NHS active ester coupling agent, and the linking of that specific binding member/coupling agent complex to a thiolated solid phase.
Figure 2:
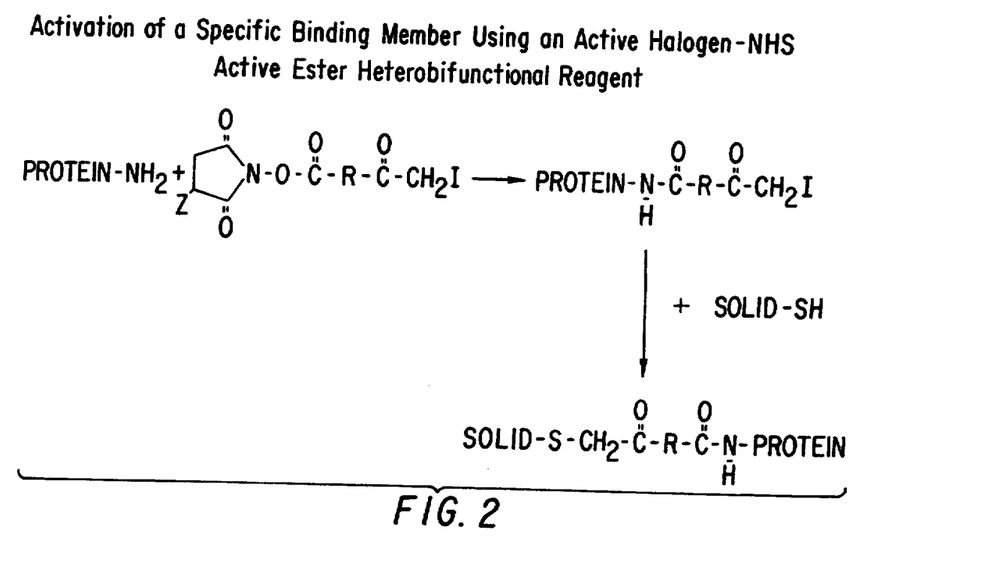
FIG. 2 is a diagrammatical illustration of the modification of an amino-bearing specific binding member to include a thiol-reactive group using an active halogen-NHS active ester coupling agent, and the linking of that specific binding member/coupling agent complex to a thiolated solid phase.

Two methods by which a specific binding member bearing an amino group can be modified to contain a thiol-reactive functional group are diagrammatically illustrated in FIGS. 1 and 2. In particular, FIG. 1 illustrates the activation of a protein specific binding member through the use of a maleimido-NHS active ester heterobifunctional reagent to incorporate a thiol-reactive group on the protein. The R in the coupling agent represents alkyl, cycloalkyl, alkyl-cycloalkyl or an aromatic carboxylic ring as described above. The Z in the coupling agent typically represents a hydrogen atom, or optionally represents an inert polar group such as $SO_3-$ which imparts the characteristic of water solubility upon the coupling agent. In a second step, the activated specific binding member is then reacted with and links to a thiolated solid phase.

Referring to FIG. 2, the specific binding member is reacted with an active halogen-NHS active ester heterobifunctional reagent, wherein R and Z are defined as described above. In a second step, the specific binding member/coupling agent complex is then reacted with and linked to a thiolated solid phase.

Figure 3:
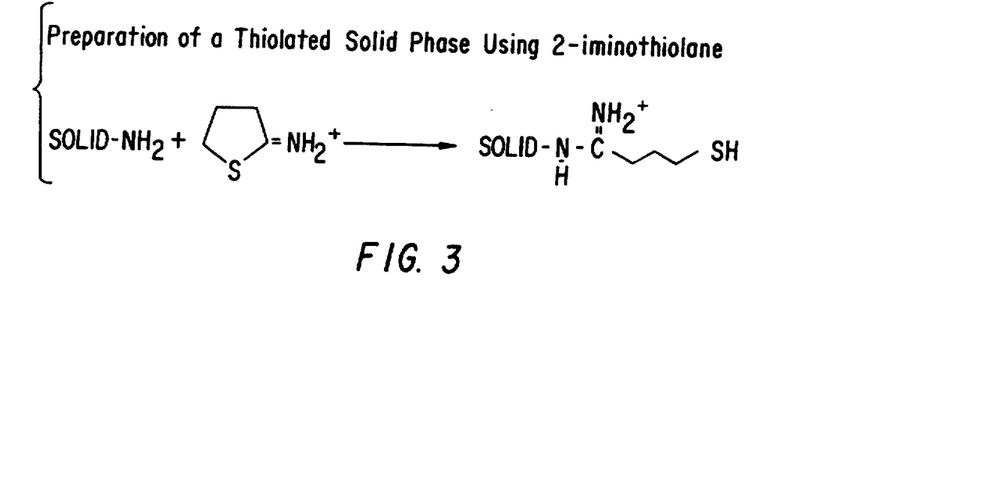
FIG. 3 is a diagrammatical illustration of the modification of an amino-bearing solid phase to include a thiol-reactive group using 2-iminothiolane.

Methods for introducing thiol groups to the solid phase, such as an aminated or carboxylated polystyrene latex particle, are diagrammatically illustrated in FIGS. 3 through 6. FIG. 3 represents the use of a thiol introducing agent, e.g., 2-iminothiolane, which is reacted with the aminated solid phase to form a thiolated solid phase.

Figure 4:
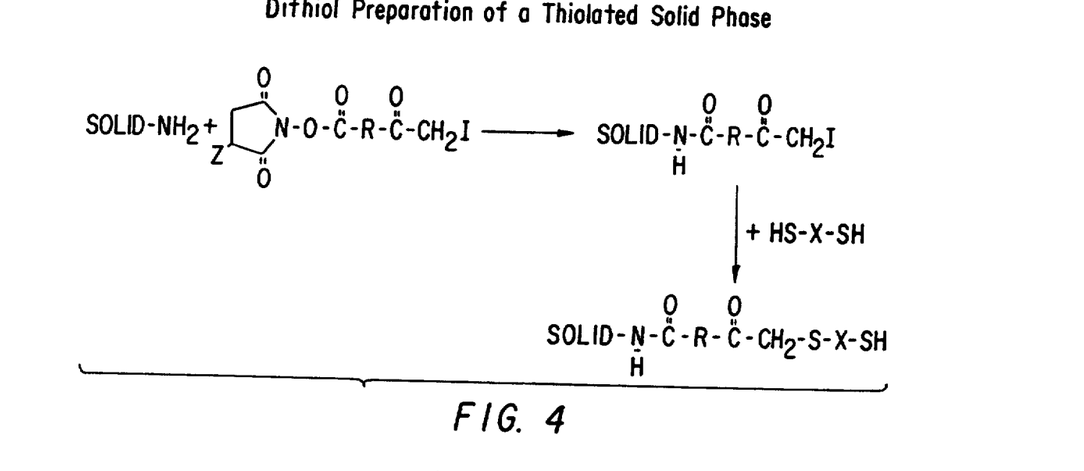
FIG. 4 is a diagrammatical illustration of the modification of an amino-bearing solid phase with a dithiol compound i:to form a thiolated solid phase.

FIG. 4 represents the reaction of an aminated solid phase with an active halogen-NHS active ester heterobifunctional reagent, wherein R and Z are defined as described above and I is a sample halogen. The resultant solid phase/coupling agent complex is then activated by reacting the complex with a thiol introducing agent, e.g., a dithiol compound represented by HS—X—SH, to produce a thiolated solid phase. As with the preparation of the specific binding member/coupling agent complex in FIG. 1, a thiolated solid phase/coupling agent complex can also be prepared through the use of a maleimido-NHS active ester heterobifunctional reagent.

Figure 5:
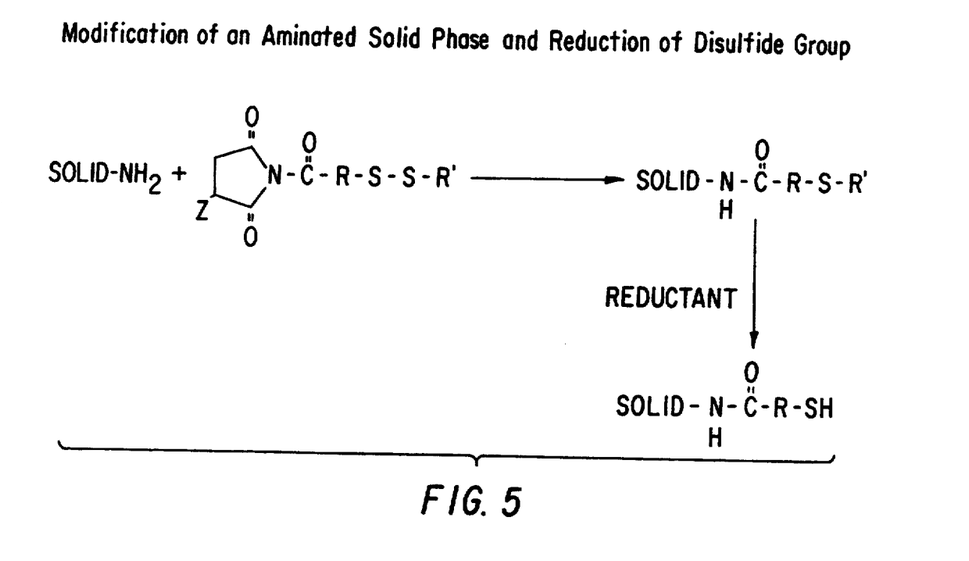
FIG. 5 is a diagrammatical illustration of the preparation of a thiolated solid phase through the reduction of a disulfide group.
Figure 6:
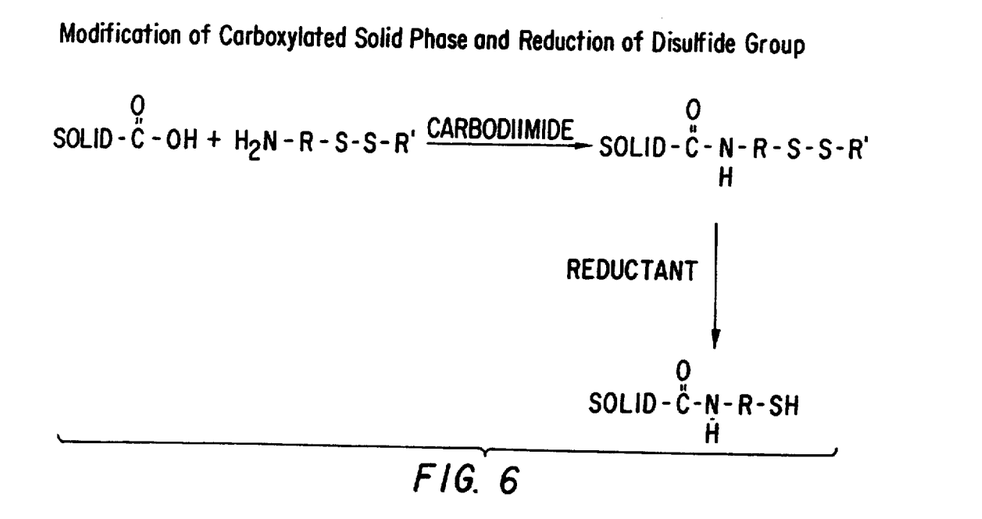
FIG. 6 is a diagrammatical illustration of the modification of a carboxylated solid phase and the reduction of a disulfide group to form a thiolated solid phase.

FIGS. 5 and 6 represent the use of disulfide compounds to modify either an aminated or carboxylated solid phase. R and Z are defined as described above. Following the reaction of the disulfide compound with the solid phase, the disulfide compound is reduced by the addition of a reductant to form a thiolated solid phase. The disulfide compounds are represented by the structure —R—S—S—R'. The reductants for use in the procedure include any substance capable of reducing the disulfide group to a thiol. Thus, the reductants include but are not limited to, thiols, borohydrides, metal hydrides and hydrogen gas with a catalyst. As an alternative to the reaction of a carboxylated solid phase and an amino-containing disulfide compound represented in FIG. 6, the solid phase can contain or be activated to include the amino group and the disulfide compound can include the carboxyl group.

Both the solid phase and the specific binding member can be modified to include a coupling agent, the coupling agents providing the required amino, thiol or carboxyl groups. One of the modified components, such as the solid phase/coupling agent complex, is then treated with a dithiol compound to introduce sulfhydryl groups to the component thereby forming a thiolated solid phase/coupling agent complex. Finally, the specific binding member/coupling agent complex is added to the thiolated solid phase/coupling agent complex to form a crosslinked product.

Figure 7:
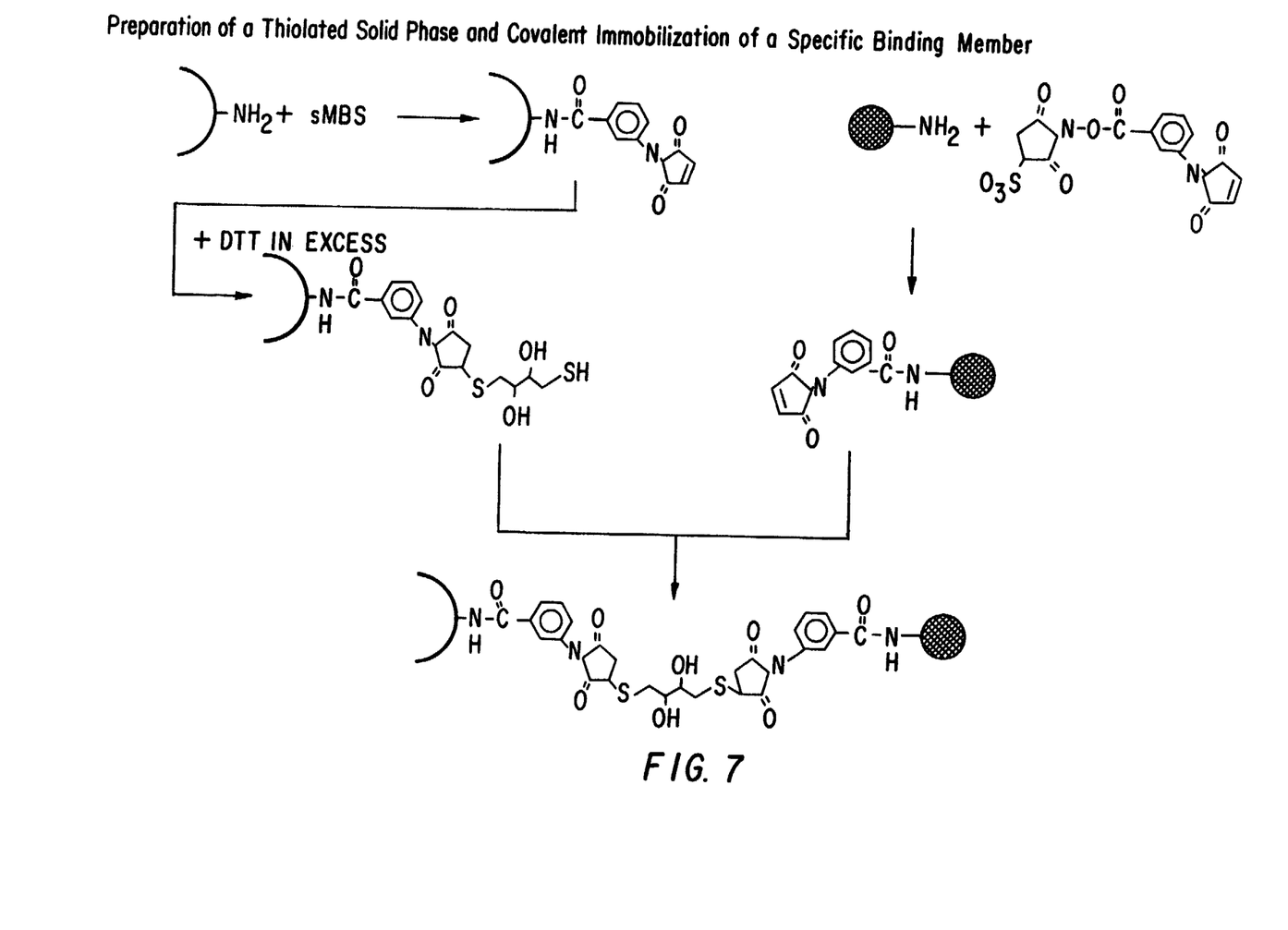
FIG. 7 is a diagrammatical illustration of the sulfhydryl crosslinking of a thiolated solid phase/coupling agent complex and a specific binding member/coupling agent complex to form an immobilized specific binding member.

An example of the sulfhydryl linkage of a specific binding member/coupling agent complex and a solid phase/coupling agent complex is diagrammatically illustrated in FIG. 7. An aminated microparticle is represented in the upper left portion of the illustration. The solid phase microparticles include commercially available latex microparticles bearing amino groups, as well as microparticles which have been modified or activated to contain amino groups. The microparticles are mixed with a heterobifunctional coupling agent, e.g., sulfo-MBS, to produce a microparticle/coupling agent complex. The microparticle/coupling agent complex is then reacted with a dithiol compound, e.g., dithiothreitol (DTT), to produce a thiolated microparticle/coupling agent complex. An aminated protein, such as an amine group bearing antigen, is represented in the upper left portion of the illustration. The protein is also linked to a heterobifunctional coupling agent to produce a protein/coupling agent complex. Lastly, the thiolated microparticle/coupling agent complex and the protein/coupling agent complex are reacted to produce a dithioether crosslinked microparticle and protein, i.e., an immobilized specific binding member.

EXAMPLES

The following examples describe methods for synthesizing the novel activated solid phase products (i.e., the thiolated solid phase/coupling agent complex) and the immobilized specific binding member products of present invention.

I. Protein Immobilization Through Dithioether Linkages

Example 1

Preparation of Recombinant HIV-1 gp-41 Derivatized Microparticles a) Preparation of Thiolated Microparticles A 3.0 ml suspension of amino-microparticles (3μ diameter, 2.5% solids, Polysciences, Inc., Warrington, Pa.) was placed into a 15 ml polypropylene centrifuge tube and centrifuged at 3000 rpm for 10 minutes. The supernatant was decanted and discarded. The microparticle pellet was resuspended in 3.0 ml of 10 mM phosphate buffered saline, pH 7.2 (PBS) by vortexing until the suspension was homogeneous. A 0.3 ml solution of N-maleimidobenzoyl-N-hydroxysulfo-succinimide ester (sulfo-MBS, Pierce Chemical Co., Rockford, Ill.), 10 mg per ml PBS, was added to the microparticle suspension, and the mixture was allowed to react for 1 hour at room temperature (20°-25° C.) with end-over-end rotation. The mixture was centrifuged, and the supernatant was decanted and discarded. The maleimido-microparticle pellet was washed by resuspension in 10 ml of PBS with vortexing, centrifuging, and then decanting the supernatant. The washing process was performed three times. The microparticle pellet was then resuspended in a 10 ml solution of 0.1M dithiothreitol in PBS. The microparticle suspension was mixed at room temperature by end-over-end rotation for 1 hour. The suspension was centrifuged, and the supernatant was decanted and discarded. The thiolated microparticles were resuspended in a 10 ml solution of 0.1% (v/v) of Tween-20 in PBS, by vortexing, to achieve a homogeneous suspension. The mixture was then centrifuged, and the supernatant was discarded. The resuspension in 0.1% Tween-20/PBS, centrifugation, and supernatant decanting steps were repeated for three additional cycles. The thiolated microparticle pellet was then resuspended with PBS to a final volume of 3.0 ml. The thiolated microparticles reacted optimally when used within 3 hours of removing the dithiothreitol.

b) Activation of Recombinant HIV-1 pg41 with Sulfo-MBS

A 1.2 ml solution of 0.3 mg protein in 1.8% sodium dodecyl sulfate (SDS)/PBS (w/v) was placed in a reaction vessel. The protein specific binding member was an HIV antigen. Exemplary HIV proteins include the recombinant protein constructs such as the gp24 and gp41 sequences disclosed in co-owned and copending U.S. patent application Ser. Nos. 020,282 (filed Feb. 27, 1987) and 811,240 (filed Dec. 20, 1985) which are herein incorporated by reference. A 1.0 ml solution of 30% Tween-20 in PBS (v/v) was added, and the solution mixed, followed by the addition of 20 μg sulfo-MBS in 0.8 ml PBS to produce a specific binding member/coupling agent complex. The solution was again mixed and allowed to set at room temperature for 1 hour.

c) Covalent Linking of Maleimidobenzoyl Activated HIV-1 gp41 to Thiolated Microparticles The activated protein (3.0 ml from Example 1. b) was combined with the suspension of thiolated microparticles (3.0 ml from Example 1. a). The mixture was allowed to react at room temperature overnight (14 to 18 hours) while rotating end-over-end. The protein coated microparticle suspension was centrifuged, as described in Example 1. a, and the supernatant was decanted and discarded. The pellet was resuspended in 10 ml of 10 mM 2-mercaptoethanol by vortexing, and the mixture was then rotated end-over-end for 1 hour. The suspension was centrifuged and the supernatant discarded. The microparticle pellet was washed by 4 cycles of resuspension in 10 ml of 0.1% Tween-20 in PBS (v/v), centrifugation, and then decanting the supernatant. The particles were then resuspended in PBS with 0.1% sodium azide (w/v) to 10 ml of a 0.75% solids suspension. The immobilized specific binding member preparation was stored at 4° to 8° C.

Example 2

Preparation of Recombinant HIV-1 p24 Coated Microparticles a) Activation of Recombinant HIV-1 p24 with Sulfo-MBS A solution of 375 μg p24 in 0.5 ml of 0.5% SDS/PBS (w/v) was heated at 45° C. for 20-30 minutes. After heating, additions of 0.5 ml of 30% Tween-20 in PBS (v/v) and 0.5 ml of PBS containing 60 μg sulfo-MBS were made to the protein solution. The reaction mixture was vortexed and set at room temperature for 1 hour to produce the specific binding member/coupling agent complex.

b) Covalent Coupling of Derivatized p24 to Thiolated Microparticles

A suspension of 3.0 ml of thiolated microparticles (as described in Example 1. a) was centrifuged and the supernatant discarded. The pellet was resuspended in the activated p24 solution with vortexing, and was mixed by end-over-end rotation at 20°14 25° C. for 14-18 hours. The suspension was then centrifuged, and the supernatant discarded. The p24 coated microparticle pellet was resuspended in 10 ml of 10 mM 2-mercaptoethanol and mixed by end-over-end rotation at 20°-25° C. for 1 hour. The suspension was again centrifuged and the supernatant discarded. The pellet was then washed with 4 cycles of resuspension in 10 ml of 0.1% Tween-20 in PBS (v/v), centrifugation, and discarding the supernatant. The pellet was resuspended in PBS containing 0.1% sodium azide (w/v) to a volume of 10 ml, and the immobilized specific binding member was stored at 4°-8° C.

Example 3

Preparation of Recombinant HIV Protein-Coated Microparticles Using Urea Activation of the Protein a) Activation of Recombinant HIV Protein with Sulfo-MBS A solution of 600 μg of HIV protein in 55 μl of 8M urea was placed in an appropriate vessel. To this, 40 μg of sulfo-MBS in 40 μl of 8M urea were added. The solution was thoroughly mixed and set at room temperature for 1 hour.

b) Covalent Coupling of Recombinant HIV Protein to Thiolated Microparticles

Activated protein, from Example 3. a, was added to a 3.0 ml suspension of thiolated microparticles from Example 1. a. The suspension was incubated at 20°-25° C. for 14-18 hours with end-over-end rotation. The protein coated microparticles were then centrifuged, treated with 2-mercaptoethanol, washed, resuspended, and stored substantially in accordance with the procedure described in Example 1. c.

II. Protein Immobilization Through Dithioether Linkages Using Alternate Heterobifunctional Reagents in Microparticle Thiolation Example 4

Preparation of Recombinant HIV-1 gp41 Derivatized Microparticles Using Sulfo-SMCC in Microparticle Thiolation The immobilized specific binding member was made substantially in accordance with the protocol described in Example 1 using sulfo-SMCC coupling agent (Pierce) instead of sulfo-MBS in the preparation of the thiolated microparticles.

Example 5

Preparation of Recombinant HIV-1 gp41 Derivatized Microparticles Using sulfo-SIAB in Microparticle Thiolation The immobilized specific binding member was made substantially in accordance with the protocol described in Example 1 using sulfo-SIAB (Pierce) instead of sulfo-MBS in the preparation of thiolated microparticles.

Example 6

Preparation of Recombinant HIV-1 gp41 Derivatized Microparticles Using SIAB in Microparticle Thiolation A 3.0 ml suspension of amino-microparticles was centrifuged at 3000 rpm for 10 minutes. The supernatant was removed and discarded. The pellet was resuspended in 3.0 ml of a 1:1 mixture of PBS and dimethylsulfoxide (DMSO) by vortexing. A 0.3 ml solution containing 3.0 mg SIAB (Pierce) in DMSO was added to the suspension which was then mixed by end-over-end rotation at 20°-25° C. for one hour. The suspension was centrifuged and the supernatant discarded. The iodoacetyl microparticles were washed using 3 cycles of resuspension in 10 ml of PBS, centrifugation, and removal of the supernatant. The pellet was then resuspended in a 10 ml solution of 0.1M dithiothreitol in PBS. The suspension was mixed for one hour at 20°-25° C., then centrifuged and the supernatant discarded. The thiolated microparticles were washed as described above using 4 cycles with 10 ml of 0.1% Tween-20 in PBS (v/v) in each cycle. The particles were then resuspended in 10 ml of PBS. The preparation of the protein/coupling agent complex and its crosslinking to the thiolated microparticles were repeated substantially in accordance with the procedures of Example 1. *b* and *c*.

Example 7

Preparation of Recombinant HIV-1 gp41 Derivatized Microparticles Using SMCC in Microparticle Thiolation

The immobilized specific binding member was made substantially in accordance with the protocol described in Example 6 using SMCC (Pierce) instead of SIAB in the preparation of thiolated microparticles.

Example 8

Preparation of Recombinant HIV-1 gp41 Derivatized Microparticles Using a 16 Atom Heterobifunctional Linker Group in Microparticle Thiolation

The immobilized specific binding member was made substantially in accordance with the protocol described in Example 6 using the 16 atom maleimido-n-hydroxysuccinimidyl active ester compound described in co-owned and co-pending U.S. patent application Ser. Nos. 254,288 and 114,930 instead of SIAB.

Example 9

Preparation of Recombinant HIV-1 gp41 Derivatized Microparticles Using a 23 Atom Heterobifunctional Linker Group in Microparticle Thiolation

The immobilized specific binding member was made substantially in accordance with the protocol described in Example 6 using the 23 atom maleimido-n-hydroxysuccinimidyl active ester compound described in U.S. patent application Ser. Nos. 254,288 and 114,930 instead of SIAB.

Example 10

Preparation of Recombinant HIV-1 gp41 Derivatized Microparticles Using a 30 Atom Heterobifunctional Linker Group in Microparticle Thiolation

The immobilized specific binding member was made substantially in accordance with the protocol described in Example 6 using the 30 atom maleimido-n-hydroxysuccinimidyl active ester compound described in U.S. patent application Ser. Nos. 254,288 and 114,930 instead of SIAB.

III. Protein Immobilization Through Dithioether Linkages Using Alternate Heterobifunctional Reagents in Protein Activation

Example 11

Preparation of Recombinant HIV-1 gp41 Derivatized Microparticles Using Sulfo-SMCC Activated gp41

The immobilized specific binding member was made substantially in accordance with the protocol of Example 1 using sulfo-SMCC instead of sulfo-MBS in the activation of recombinant gp41 described in Example 1. *b*.

Example 12

Preparation of Recombinant HIV-1 gp41 Derivatized Microparticles Using sulfo-SIAB Activated gp41

The immobilized specific binding member was made substantially in accordance with the protocol of Example 1 using sulfo-SIAB instead of sulfo-MBS in the activation of recombinant gp41 described in Example 1. *b*.

Example 13

Preparation of Recombinant HIV-1 gp41 Derivatized Microparticles Using SMCC Activated gp41

A 1.0 ml solution of 0.3 mg protein in PBS was mixed with 2.0 ml of DMSO containing 20 $\mu$g of SMCC. The solution was mixed and set at 20°-25° C. for 1 hour to produce the specific binding member/coupling agent complex. The preparation of thiolated microparticles and the protein-to-microparticle coupling procedures were repeated as described in Example 1 *a* and *c*, respectively.

Example 14

Preparation of Recombinant HIV-1 gp41 Derivatized Microparticles Using SIAB Activated gp41

The immobilized specific binding member was made substantially in accordance with the protocol described in Example 13 using SIAB instead of SMCC in the derivatization of recombinant gp41.

Example 15

Preparation of Recombinant HIV-1 gp41 Derivatized Microparticles Using a 30 Atom Heterobifunctional Linker Modified gp41

The immobilized specific binding member was made substantially in accordance with the protocol described in Example 13 using the 30 atom maleimido-n-hydroxysuccinimidyl active ester compound, described in U.S. patent application Ser. Nos. 254,288 and 114,930 instead of SMCC in the activation of recombinant gp41.

IV. Protein Immobilization with Microparticles Thiolated by 2-Iminothiolane

Example 16

Covalent Binding of Recombinant HIV-1 gp41 to Microparticles Thiolated by 2-Iminothiolane a) Preparation of Thiolated Microparticles

A 3.0 ml suspension of amino-microparticles (3$\mu$ diameter, 2.5% solids in deionized water; Polysciences Inc.) was added to a 15 ml, ice cold solution of 50 mM N-methylmorpholine, pH 6.5. To this was added 9.0 ml of ice cold 0.1M sodium bicarbonate containing 90 mg of 2-iminothiolane (Pierce Chemical Co.). The suspension was mixed at room temperature (20°-25° C.) for one hour by continuous rotation, centrifuged at 4,500 rpm for 10 minutes, and the supernatant was removed and discarded. The pellet was washed by 3 cycles of resuspending in 30 ml of 0.05% Tween-20 in PBS (v/v) with vortexing, centrifuging, and discarding the supernatant. The thiolated microparticles were left as a pellet, and used within 1 hour.

b) Activation of Recombinant HIV-1 gp41 with sulfo-MBS

A 2.0 ml solution of PBS containing 20 $\mu$g of sulfo-MBS was added to a 1.0 ml solution of 250 $\mu$g of gp41 in deionized water for the preparation of the specific binding member/coupling agent complex. The mixture was vortexed, then set at room temperature for 1 hour.

c) Covalent Coupling of Derivatized gp41 to Thiolated Microspheres

The activated protein solution, of Example 16. *b*, and 2.0 ml of PBS were added to the thiolated microsphere pellet of Example 16. *a*. The particles were resuspended with vortexing and the suspension was mixed by end-over-end rotation at 20°–25° C. for 14–18 hours. The suspension was centrifuged, treated with 2-mercaptoethanol, washed, resuspended, and stored substantially in accordance with the protocol described in Example 1. c.

Example 17

Preparation of Peptide Derivatized Microparticles Using 2-Iminotholane for Microparticle Thiolation A solution of 430 μg of an amine containing synthetic peptide (20–30) amino acid residues) in 150 μl of PBS was added to 3.0 ml of thiolated microparticles, prepared as described in Example 16. a. To this suspension, 75 μl of a 1 mg SIAB per ml methanol solution was added, and the mixture was rotated end-over-end at 20°–25° C. for 14–18 hours. The derivatized microparticles were then centrifuged, washed, resuspended, and stored substantially in accordance with the protocol described in Example 1. c.

V. Protein Immobilization with Microparticles Thiolated Using Disulfides

Example 18

Preparation of Recombinant HIV-1 gp41 Derivatized Microparticles Using SPDP in Microparticle Thiolation The immobilized specific binding member was made substantially in accordance with the protocol described in Example 6 using SPDP (Pierce) instead of SIAB in the preparation of the thiolated microparticles.

Example 19

Covalent Binding of Recombinant HIV-1 gp41 to N-(5-dimethylaminonaphthalene-1-sulfonyl)-cysteine (Dansyl-cys) Derivatized Microparticles A 5.0 ml solution of 10 mg/ml N,N'-didansyl-L-cystine (Sigma, St. Louis, Mo.) in 1:1, DMSO:5 mM 2-(N-Morpholino)-ethanesulfonic acid (MES, Sigma), pH 5.0 was added to a 5.0 ml suspension of amino-microparticles. Five milligrams of 1-Ethyl-3-(3-Dimethyl-aminopropyl) carbodiimide hydrochloride (EDC, Pierce) in 0.5 ml deionized water were added to the microparticle suspension. The mixture was rotated, end-over-end, at 20°–25° C for 2 hours. A second aliquot of 5 mg EDC in 0.5 ml deionized water was added, and the suspension was rotated another 2 hours. The derivatized microparticles were centrifuged, and the supernatant was discarded. The pellet was then resuspended in 15 ml of 0.1M dithiothreitol and rotated, end-over-end, for 1 hour. The suspension was centrifuged, and the supernatant was decanted and discarded. The thiolated microparticles were washed with 4 cycles of resuspending in 15 ml of 0.1% Tween-20 in PBS, centrifuging, and discarding the supernatant. The pelleted microparticles were then resuspended to a volume of 5.0 ml with PBS. The preparation of the gp41 specific binding member/coupling agent complex and its crosslinking to the thiolated microparticles were repeated substantially in accordance with the protocol described in Example 1. b and c.

Example 20

Covalent Binding of Recombinant HIV-1 gp41 to Mercaptoethylamine Derivatized Microparticles a) Preparation of Mercaptoethylamine Derivatized Microparticles A 0.6 ml suspension of carboxylated microparticles (0.49μ diameter, 2.5% solids, Polysciences) was centrifuged at 10,000×g for 5 minutes. The supernatant was aspirated and discarded. The pellet was resuspended in 1.0 ml of 0.1M cystamine (Sigma), 5 mM MES, pH 5.0. A 0.2 ml solution containing 2 mg EDC in deionized water was added to the suspension, which was then vortexed and rotated, end-over-end, at 20°–25° C. for 14–18 hours. The suspension was centrifuged, and the supernatant was discarded. The cystamine derivatized microparticles were then washed with 3 cycles of resuspending in 1.0 ml of 0.1% Tween-20 in PBS, centrifuging, and discarding the supernatant. The pellet was then resuspended in 1.0 ml of 0.1 M dithiothreitol in PBS and rotated, end-over-end, at 20°–25° C. for 1 hour. The suspension was centrifuged, the supernatant discarded, and the mercaptoethylamine derivatized microparticles were washed as described above. The pellet was then resuspended with 0.6 ml of PBS.

b) Covalent Linking of Maleimidobenzoyl Activated HIV-1 gp41 to Thiolated Microparticles The protein was activated substantially in accordance with the protocol described in Example 1. b. A 0.3 ml aliquot of the gp41 specific binding member/coupling agent complex was added to 0.3 ml of the mercaptoethylamine derivatized microparticles from Example 20. a. The suspension was mixed by vortexing, then rotated, end-over-end, at 20°–25° C. for 14–18 hours. The suspension was centrifuged, and the supernatant was aspirated and discarded. The pellet was resuspended in 1.0 ml of 10 mM 2-mercaptoethanol and rotated, end-over-end, for 1 hour. The suspension was centrifuged, the supernatant discarded, and the protein coated microparticles were washed with 4 cycles of resuspending in 1.0 ml of 0.1% Tween-20 in PBS, centrifuging, and discarding the supernatant. The microparticles were resuspended in 1.0 ml of PBS and stored at 4° to 8° C.

Example 21

Covalent Binding of Recombinant HIV-1 gp41 to L-Cysteine-O-methyl Ester Derivatized Microparticles The immobilized specific binding member was made substantially in accordance with the protocol described in Example 20 using L-cystine dimethylester dihydrochloride (Sigma) instead of cystamine to prepare the microparticles.

It will be appreciated by one skilled in the art that the concepts of the present invention are equally applicable to the crosslinking of many other specific binding members, solid phase materials and coupling agents. The embodiments described herein are intended as examples rather than as limitations. Thus, the description of the invention is not intended to limit the invention to the particular embodiments described in detail, but it is intended to encompass all equivalents and subject matter within the spirit and scope of the invention as described above and as set forth in the following claims.

What is claimed is:

1. An immobilized specific binding member, comprising a compound of the formula:

wherein B is a solid phase having a reactive member selected from the group consisting of amino, carboxyl and thiol groups;

M is a specific binding member having an amino group;

R and R' are coupling agents independently selected from the group consisting of heterobifunctional and homobifunctional reagents; and X is a dithio compound linked to R through a thioether and to R' through a thioether; wherein R is attached to B via the amino, carboxyl or thiol group of B, and R' is attached to M via the amino group of M.

2. The immobilized specific binding member according to claim 1, wherein said solid phase is selected from the group consisting of particles, tubes, sheets, plates, slides, wells and tapes.

3. The immobilized specific binding member according to claim 1, wherein R and R' are heterobifunctional coupling agents, both of which are the same.

4. The immobilized specific binding member according to claim 1, wherein said coupling agents are independently selected from the group consisting of maleimido-N-hydroxysuccinimide active esters and active halogen-N-hydroxysuccinimide active esters.

5. The immobilized specific binding member according to claim 4, wherein at least one coupling agent is a maleimido-N-hydroxysuccinimide ester selected from the group consisting of m-maleimidobenzoyl-N-hydroxy-succinimide ester; succinimidyl 4-(N-maleimidomethyl)cyclohexane-1-carboxylate; succinimidyl 4-(p-maleimidophenyl)butyrate; m-maleimidobenzoylsulfosuccinimide ester; and sulfosuccinimidyl 4-(p-maleimidophenyl)butyrate.

6. The immobilized specific binding member according to claim 4, wherein at least one coupling agent is a maleimido-N-hydroxysuccinimide active ester having a spacer represented by the formula:

$$-(X_n)-C(=O)-R$$

wherein X is a substituted or unsubstituted amino acid having from three to ten carbon atoms in a straight chain;

n is from one to ten; and

R is an alkyl, cycloalkyl, alkyl-cycloalkyl or an aromatic carboxylic ring.

7. The immobilized specific binding member according to claim 4, wherein at least one coupling agent is an active halogen-N-hydroxysuccinimide active ester selected from the group consisting of N-succinimidyl bromoacetate, N-succinimidyl (4-iodoacetyl) aminobenzoate and sulfosuccinimidyl (4-iodoacetyl)aminobenzoate.

8. The immobilized specific binding member according to claim 1, further comprising a support medium for supporting the immobilized specific binding member.

9. The immobilized specific binding member according to claim 1, wherein said solid phase is a latex microparticle and wherein said specific binding member is an antigen.

10. The immobilized specific binding member according to claim 1, wherein said solid phase is an aminopolystyrene microparticle and wherein said specific binding member is an HIV antigen.

11. The immobilized specific binding member according to claim 1, wherein said specific binding member is one member of an immunoreactive specific binding pair.

12. The immobilized specific binding member according to claim 1, wherein said specific binding member is selected from the group consisting of a polynucleotide and a polypeptide.

13. A method for producing an immobilized specific binding member, comprising the steps of:

a. reacting a solid phase, having a reactive member selected from the group consisting of amino, carboxyl and thiol groups, with a first coupling agent selected from the group consisting of heterobifunctional and homobifunctional reagents having a first function reactive with the reactive member of said solid phase and a second function reactive with a thiol, thereby forming a solid phase/coupling agent complex by reaction between said reactive member and first function of the first coupling agent;

b. reacting a specific binding member having an amino group with a second coupling agent having a first function reactive with said amino group and a second function reactive with a thiol, thereby forming a specific binding member/coupling agent complex by reaction between said amino group and first function of the second coupling agent; and c. reacting said solid phase/coupling agent complex and said specific binding member/coupling agent complex with a dithiol compound thereby forming a solid phase/specific binding member complex wherein the solid phase and the specific binding member are coupled together through two thioethers.

14. The method of claim 13, wherein said solid phase is selected from the group consisting of particles, tubes, sheets, plates, slides, wells and tapes.

15. The method according to claim 13, wherein said first and second coupling agents are heterobifunctional reagents.

16. The method according to claim 13, wherein said coupling agents are independently selected from the group consisting of maleimido-N-hydroxysuccinimide active esters and active halogen-N-hydroxysuccinimide active esters.

17. The method according to claim 16, wherein at least one coupling agent is a maleimido-N-hydroxysuccinimide ester selected from the group consisting of m-maleimidobenzoyl-N-hydroxy-succinimide ester; succinimidyl 4-(N-maleimidomethyl)cyclohexane-1-carboxylate; succinimidyl 4-(p-maleimidophenyl)butyrate; m-maleimidobenzoyl-sulfosuccinimide ester; and sulfosuccinimidyl 4-(p-maleimidophenyl) butyrate.

18. The method according to claim 16, wherein at least one coupling agent is a maleimido-N-hydroxysuccinimide active ester having a spacer represented by the formula:

$$-(X_n)-C(=O)-R$$

wherein X is a substituted or unsubstituted amino acid having from three to ten carbon atoms in a straight chain;

n is from one to ten; and

R is an alkyl, cycloalkyl, alkyl-cycloalkyl or an aromatic carboxylic ring.

19. The method according to claim 16, wherein at least one coupling agent is an active halogen-N-hydroxysuccinimide active ester selected from the group consisting of N-succinimidyl bromoacetate, N-succinimidyl (4-iodoacetyl)aminobenzoate and sulfosuccinimidyl (4-iodoacetyl)aminobenzoate.

20. The method according to claim 13, further comprising incorporating said solid phase/specific binding member complex upon or within a support medium.

21. The method according to claim 13, wherein said solid phase is a latex microparticle and wherein said specific binding member is an antigen.

22. The method according to claim 13, wherein said solid phase is an amino-polystyrene microparticle and wherein said specific binding member is an HIV antigen.

23. The method according to claim 13, wherein said specific binding member is one member of an immunoreactive specific binding pair.

24. The method according to claim 13, wherein said specific binding member is selected from the group consisting of a polynucleotide and a polypeptide.

25. The method according to claim 13, wherein said solid phase/coupling agent complex is reacted with the dithiol compound, to form a thiolated solid phase/coupling agent complex, and then the specific binding member/coupling agent complex is reacted with said thiolated solid phase/coupling agent complex.

26. The method according to claim 13, wherein said specific binding member/coupling agent complex is reacted with the dithiol compound to form a thiolated specific binding member/coupling agent complex and then the solid phase/coupling agent complex is reacted with said thiolated specific binding member/coupling agent complex.

* * * * *